US009597478B2

(12) United States Patent
Houston

(10) Patent No.: US 9,597,478 B2
(45) Date of Patent: Mar. 21, 2017

(54) INFANT SOOTHING CARRIER ASSEMBLY AND APPARATUS

(71) Applicant: Albert Daniel Houston, Boerne, TX (US)

(72) Inventor: Albert Daniel Houston, Boerne, TX (US)

( * ) Notice: Subject to any disclaimer, the term of this patent is extended or adjusted under 35 U.S.C. 154(b) by 532 days.

(21) Appl. No.: 13/890,252

(22) Filed: May 9, 2013

(65) Prior Publication Data

US 2014/0144346 A1 May 29, 2014

Related U.S. Application Data

(60) Provisional application No. 61/644,430, filed on May 9, 2012.

(51) Int. Cl.

*A61M 21/00* (2006.01)
*A61M 21/02* (2006.01)
*B62B 9/22* (2006.01)

(52) U.S. Cl.

CPC ............... *A61M 21/02* (2013.01); *B62B 9/22* (2013.01); *A61M 2021/0022* (2013.01); *A61M 2021/0027* (2013.01); *A61M 2230/04* (2013.01); *A61M 2230/06* (2013.01); *A61M 2230/40* (2013.01); *A61M 2230/50* (2013.01)

(58) Field of Classification Search

CPC ........ A61M 21/02; B62B 5/0033; B62B 7/04; B62B 7/042; B62B 7/048; B62B 9/22

See application file for complete search history.

(56) References Cited

U.S. PATENT DOCUMENTS 2,496,733 A * 2/1950 Mackie ..................... B62B 9/22 104/173.1
2,888,086 A * 5/1959 O'Brien .................... B62B 9/22 104/302
5,002,144 A * 3/1991 McMahon ................ B62B 9/22 180/166
5,435,317 A * 7/1995 McMahon ............. A61B 5/113 600/534
5,463,961 A * 11/1995 Graves .................... B61C 13/04 104/139

(Continued)

OTHER PUBLICATIONS

Fisher-Price Cruisin' Motion(TM) Soother, found at http://www.fisher-price.com/en_US/products/63394.

*Primary Examiner* — Jason C Smith
(74) *Attorney, Agent, or Firm* — Bruce E. Houston

(57) ABSTRACT

Apparatus and systems drive an infant carrier through space while providing soothing acceleration and/or sonic components. Infant-soothing swaying and vibrating mechanisms help to calm an upset infant and/or help the infant to fall asleep. Embodiments described herein include infant carriers capable of self-locomotion and/or platforms capable of self-locomotion with snap-in fasteners to accept an infant carrier. In some embodiments, a platform with an attached infant carrier travels along a track or monorail. In some embodiments, an infant carrier with wheels may be pulled by a toy providing the locomotion. Some embodiments incorporate a device controller with biofeedback mechanisms to adaptively pinpoint characteristics of soothing motions and sounds appropriate to a selected soothing task for a particular infant in a particular emotional state.

20 Claims, 12 Drawing Sheets

600
510
612
615

(56) References Cited

U.S. PATENT DOCUMENTS

| | | | | |
|---|---|---|---|---|
| 2004/0212161 | A1* | 10/2004 | Haigh | B62B 9/22 280/47.1 |
| 2005/0017469 | A1* | 1/2005 | Hill | B62B 3/144 280/47.38 |
| 2008/0124683 | A1* | 5/2008 | Medford | G09B 19/00 434/29 |
| 2011/0221148 | A1* | 9/2011 | Annese | B62B 5/067 280/47.34 |
| 2014/0250592 | A1* | 9/2014 | Karp | A47D 9/02 5/108 |
| 2015/0042076 | A1* | 2/2015 | Mills | B62B 7/145 280/650 |
| 2015/0045608 | A1* | 2/2015 | Karp | A47D 15/008 600/28 |

* cited by examiner

INFANT SOOTHING CARRIER ASSEMBLY AND APPARATUS

PRIORITY CLAIM

This application claims the benefit of priority under 35 U.S.C. §119(e) to U.S. Provisional Patent Application Ser. No. 61/644,430 titled "INFANT SOOTHING APPARATUS AND METHODS" filed on May 9, 2012 and incorporated herein by reference in its entirety.

TECHNICAL FIELD

Embodiments described herein relate to apparatus associated with infant care, including infant carrier assemblies to sooth a crying infant and/or to put an infant to sleep.

BACKGROUND INFORMATION

It is well known that soothing a tired, crying, and/or upset infant is often a challenging, time-consuming part of child rearing. This is particularly true during the first few years of a child's life, before and while learning to talk, as crying may be a baby's primary means of expression.

It has been said that infants have an uncanny ability to require whatever mode of soothing results in the greatest amount of work for the parent in any particular situation. Thus, for example, a parent may lift and cradle a crying infant in his/her arms while sitting. The infant may be comforted and stop crying for a while. Shortly, though, the infant may resume crying and require rocking or a light bouncing motion to be further consoled. Eventually, the parent may be required to transition to a standing or a walking state to further comfort the infant. Often a difficult situation frequently arises at the end of an infant's wakeful period. The baby may becomes fussy, tired, and ready to sleep, but cannot because he/she is crying. Some parents even report having to go to the extreme of taking an infant for an automobile ride to lull her/him to sleep. Doing so is apparently often effective, but may result in considerable time and expense.

As the pace of life accelerates, the time and patience required of exhausted two working-parent families to sooth infant children may contribute substantially to family stress. Various soothing aids and devices have been suggested and marketed to assist parents with the above-described burdens of parenting infant children. For example, wind-up or electric powered baby swings may entertain an infant for a period of time but are often ineffective in lulling the infant to sleep. Motion-creating infant carriers that are fixed in space, with fixed feet to be placed on the floor or on a table, for example, are known. Such products may have limited effectiveness and may be subject to habituation, as they provide insufficient diversity in both range of acceleration motion and in a target infant's field-of-view. Thus, there exists a long-felt but largely unsatisfied need for a device capable of effectively standing in for labor-intensive parental soothing when required.

INTRODUCTION

Apparatus described herein drive an infant carrier through space while providing soothing acceleration and/or sonic components. Some embodiments may incorporate biofeedback mechanisms to adaptively pinpoint characteristics of soothing motions and sounds appropriate to a selected soothing task for a particular infant in a particular emotional state. Infant caretakers may be relieved of time and energy consuming low-level soothing tasks as a result.

Embodiments described herein include infant carriers capable of self-locomotion and/or platforms capable of self-locomotion with snap-in fasteners to accept an infant carrier. In some embodiments, a platform with an attached infant carrier travels along a track or monorail. In some embodiments, an infant carrier with wheels may be pulled by a toy providing the locomotion. For example, an infant carrier with wheels may be pulled along a track by a toy train. The various embodiments employ infant-soothing swaying and vibrating mechanisms that may help to calm an upset infant and/or help the infant to fall asleep.

DETAILED DESCRIPTION

Figure 1A:
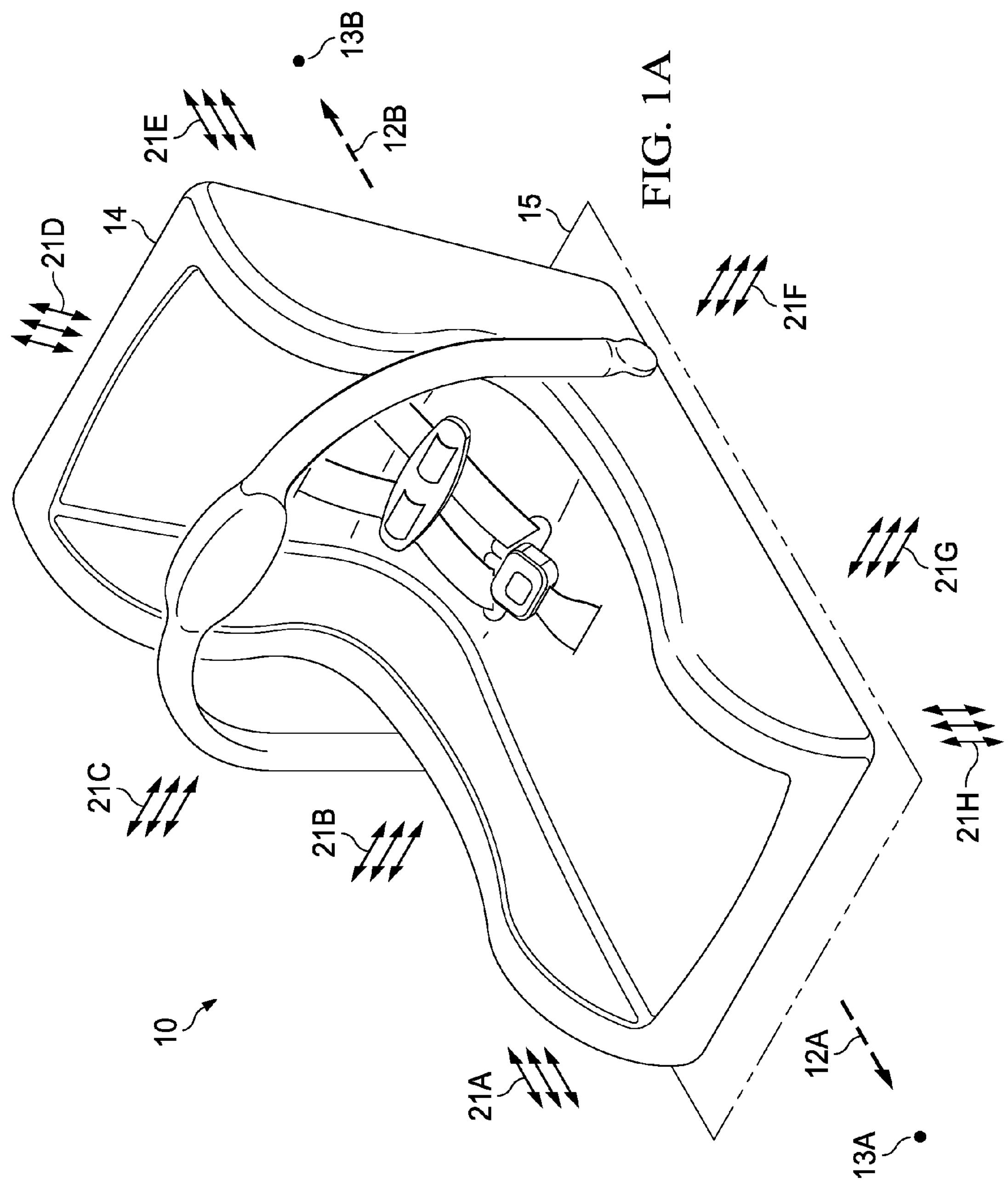
FIG. 1A is an illustration of an infant soothing carrier assembly according to various example embodiments of the invention.

FIG. 1A is an illustration of an infant soothing carrier assembly 10 according to various example embodiments of the invention. The infant soothing carrier assembly 10 is capable of self-locomotion along a path (e.g., the path 12A, 12B) between points (e.g., the points 13A, 13B) within a selected space. In addition to locomotion along the path 12A, 12B, the infant soothing carrier assembly 10 is capable of imparting soothing acceleration components (e.g. the acceleration components 21A, 21B, 21C, 21D, 21E, 21F, 21G, and 21H) in various directions in three-space.

In some embodiments, soothing acceleration component-generating apparatus may be incorporated into the infant soothing carrier assembly 10 to create or enhance one or more of the acceleration components 21A-21H. Such soothing acceleration-generating apparatus may also be referred to herein as "soothing motion-generating apparatus."

The infant soothing carrier assembly 10 includes an infant carrier 14, a platform apparatus 15, or both. In some embodiments, the infant carrier 14 may be mounted on the platform apparatus 15. In some embodiments, the platform apparatus 15 may be adapted to accept and to fasten-in an infant carrier such as the infant carrier 14. The infant carrier 14, the platform apparatus 15, or both may include motion-enabling components such as a set of wheels. In some embodiments the platform apparatus 15 may incorporate a toy such as a toy train, or decorative portions thereof.

Figure 1B:
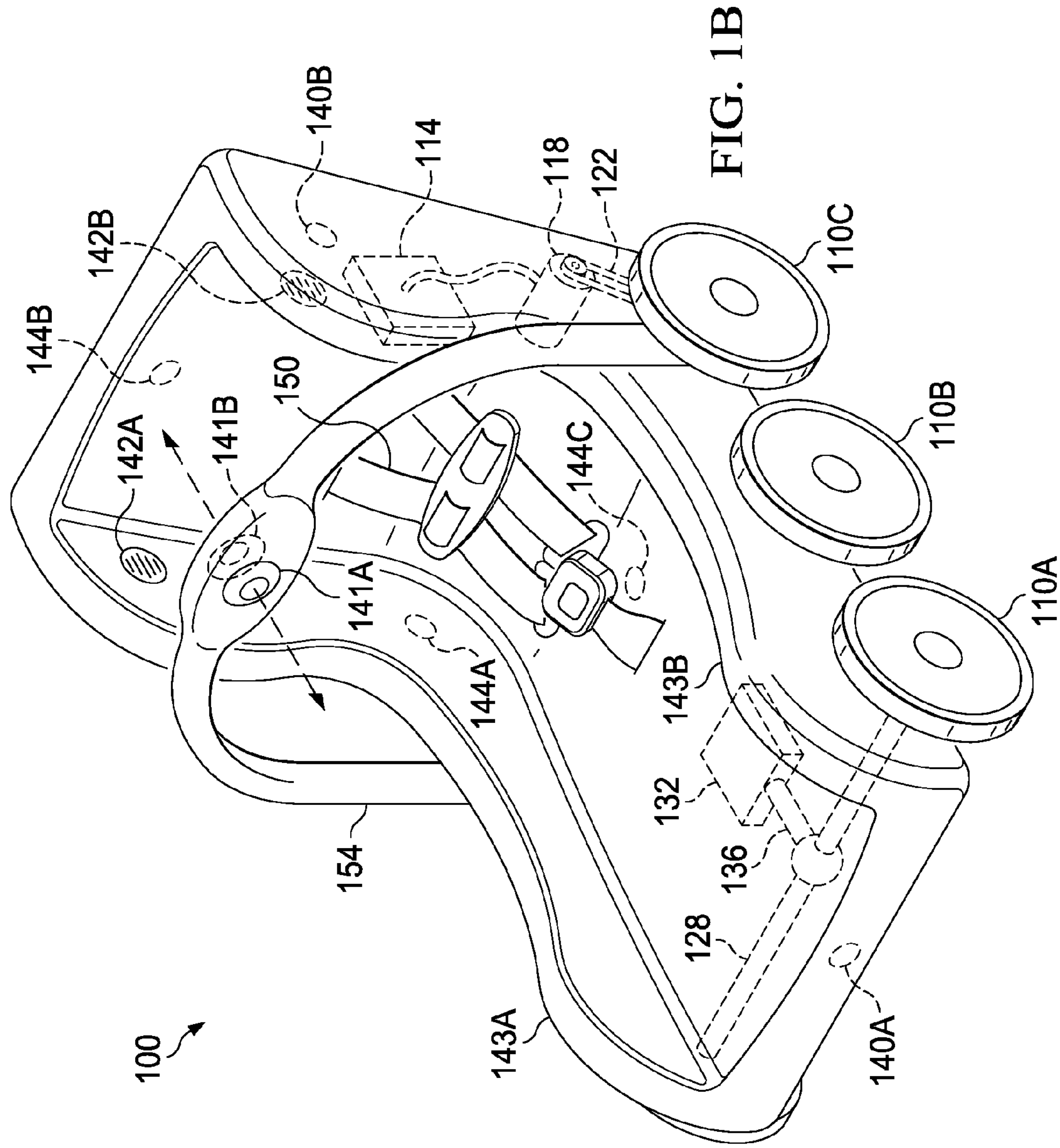
FIG. 1B is an illustration of an infant soothing carrier assembly according to various example embodiments.

FIG. 1B is an illustration of an infant soothing carrier assembly 100 according to various example embodiments. The carrier assembly 100 includes wheels (e.g., wheels 110A, 110B, and 110C) and is capable of self-locomotion along a path between points within a selected space It is noted that, although the example embodiment of FIG. 1B includes six wheels, some embodiments may include a greater or fewer number of wheels.

In some embodiments, the soothing carrier assembly 100 may be powered by a battery 114 affixed to or enclosed within the soothing carrier assembly 100. The battery 114 is electrically coupled to an electric motor 118, the latter also housed within or upon the soothing carrier assembly 100. The electric motor 118 drives one or more of the wheels 110 via a drivetrain 122. The drivetrain 122 may include one or more gears, pulleys, belts, etc. In some embodiments, one or more of the wheels 110 may each be directly driven by a wheel-specific motor (not shown in FIG. 1B) coupled to the corresponding wheel.

The soothing carrier assembly 100 also includes a steering mechanism 128 (e.g., rack and pinion steering linkage or similar steering mechanisms as are known in the vehicular arts). The steering mechanism 128 is coupled to the front set of wheels, the rear set of wheels, or both.

The soothing carrier assembly 100 may also include a soothing carrier assembly device controller 132 housed within or upon the soothing carrier assembly 100. The carrier assembly device controller 132 is electrically coupled to the electric motor 118 and/or to wheel-specific motors (not shown in FIG. 1B). The device controller 132 determines the path along which the soothing carrier assembly 100 is to travel. In some embodiments, a mechanical linkage 136 communicatively couples the controller 132 to the steering mechanism 128.

In some embodiments, the controller 132 may effect or fine-tune steering operations by sending appropriate signals to one or more intermediate electromechanical devices such as servos, solenoids, and the like (not shown in FIG. 1B) coupled to the steering mechanism 128 or to pivoting versions of the wheels 110. The intermediate electromechanical devices move the steering mechanism 128 and/or the wheels 110 responsive to control signals from the controller 132. In the case of embodiments utilizing a separate motor for each of the wheels 110, the controller 132 may effect steering by causing one or more of the wheels 110 to rotate at rates different from the rate of rotation of the other wheels 110.

In some embodiments, the controller 132 may be programmed to drive the soothing carrier assembly 100 along a predetermined path. Some embodiments may include one or more sensors (e.g., the sensors 140A and 140B) coupled to the soothing carrier assembly 100. The sensors 140 may sense the proximity of the soothing carrier assembly 100 to other objects. The controller 132 accepts inputs from the sensors 140 and may use information from the sensor signals for path determination, collision avoidance, etc.

The soothing carrier assembly 100 may also include one or more outward facing camera(s) 141A affixed to or integrated into the carrier assembly 100 and communicatively coupled to the device controller 132. The outward facing cameras 141A may be video or frame-on-demand based cameras. The cameras 141A provide image information to object feature recognition mechanisms incorporated into the controller 132. Such object feature recognition mechanisms may extract features of the surroundings of the soothing carrier assembly 100 as an adjunct to determining the current location of the carrier assembly 100 relative to surrounding objects.

The soothing carrier assembly 100 may further include one or more infant-facing camera(s) 141B coupled to the device controller 132. The infant-facing cameras 1B may be a video camera or a frame-on-demand based camera. The cameras 141B may be communicatively coupled to the device controller 132 to provide image information to infant feature recognition mechanisms incorporated into the device controller 132. The controller 132 may use the infant feature information so derived (e.g., smiles, frowns, fearful expressions, a sleepy face, etc.) as an adjunct to determining the current emotional state of the infant. The infant-facing cameras 141B may also provide a wireless video feed to a caretaker for child monitoring purposes.

The soothing carrier assembly 100 may also include audio output transducers 142A and 142B such as speakers. The speakers 142 are positioned at the upper inside portions of the left and right lateral carrier members 143A and 143B. The controller 132 sends soothing sound signals to the speakers 142.

Physiological telemetry sensors (e.g., sensors 144A, 144B, and 144C) coupled to the device controller 132 may take vital sign measurements of the infant riding in the carrier assembly 100 during operation. Such measurements may include body temperature, electrocardiographic data, respiratory data, electroencephalographic data, etc. The controller 132 compiles data from the telemetry sensors 144 and may thereby determine components of the infant's emotional state, including the infant's state of wakefulness. Via this mechanism, a caretaker may be remotely alerted that the infant has fallen asleep.

The soothing carrier assembly 100 also includes safety apparatus such as a safety harness 150 and one or more roll bars 154 coupled to the soothing carrier assembly 100.

Figure 2:
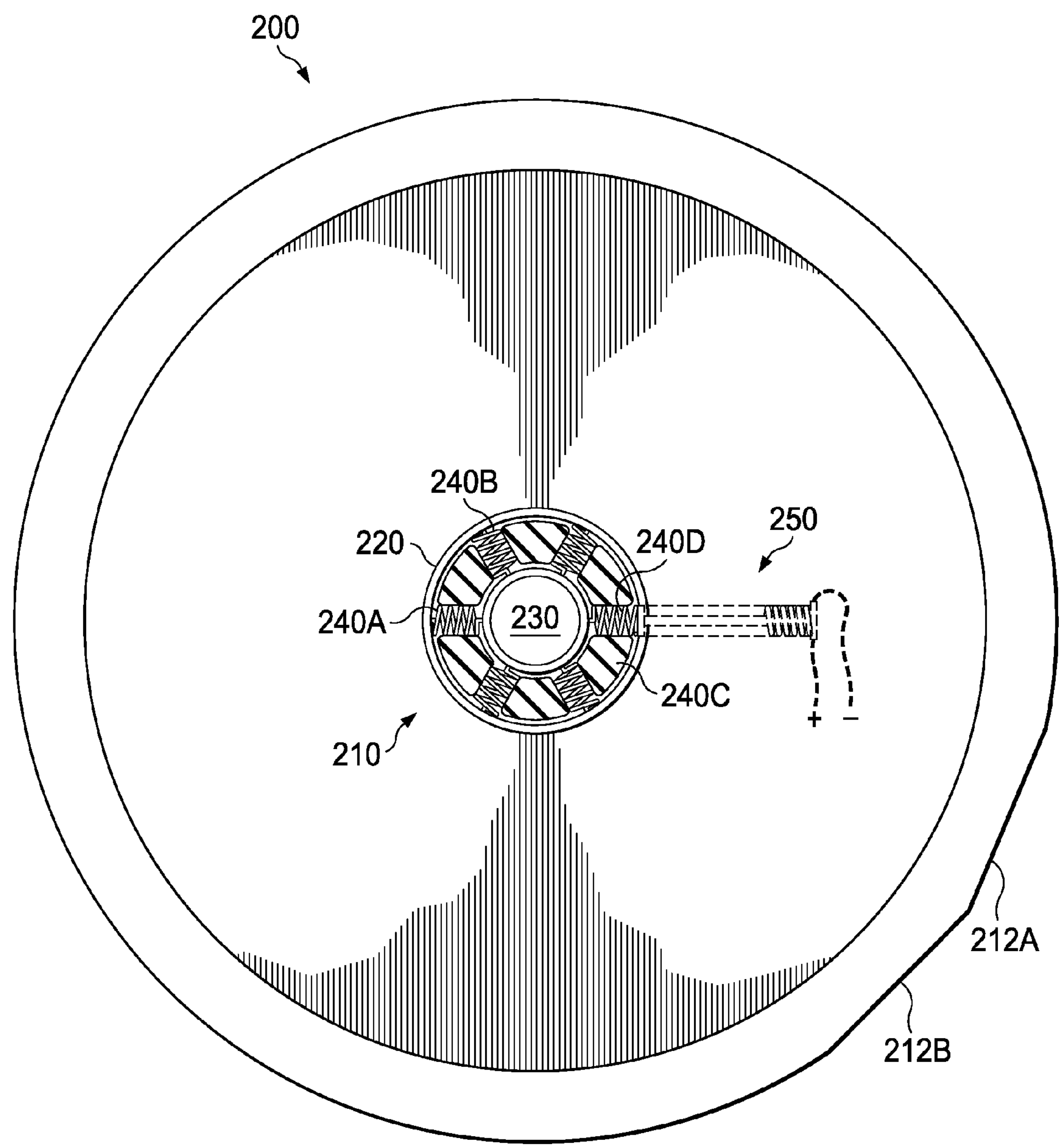
FIG. 2 is a cross-sectional diagram of a wheel with a swaying apparatus according to various example embodiments.

FIG. 2 is a cross-sectional diagram of a wheel 200 with a swaying apparatus 210 according to various example embodiments. The swaying apparatus 210 imparts soothing lateral acceleration components (e.g., the acceleration components 21A-21H of FIG. 1A). In some embodiments, wheels such as the wheel 200 may be implemented as the wheels 110 of the soothing carrier assembly 100 of FIG. 1B. In some embodiments, the outer circumference of the wheel 200 may have flat or irregular portions or segments (e.g., the flat/irregular segments 212A and 212B). Such irregularities in the wheel 200 may contribute soothing vertical acceleration components in the form of a bouncing effect to the soothing carrier assembly 100.

The swaying apparatus 210 includes an outer hub 220 coupled to the wheel 200. The swaying apparatus 210 also includes an inner hub 230 flexibly coupled to the outer hub 220. In some embodiments, one or more flexible members 240 are coupled between the outer hub 220 and the inner hub 230. The flexible members 240 may include a set of springs (e.g., the springs 240A and 240B) and/or a flexible material 240C such as rubber. The flexible members 240 provide both radial and axial flexibility between the outer hub 220 and the inner hub 230. Such flexibility imparts a swaying motion at the soothing carrier assembly 100.

Some embodiments of the swaying apparatus 210 may also include a swaying motion modulation device 250 coupled to one or more of the flexible members 240. The swaying motion modulation device 250 may include one or more solenoids, servos, etc. to compress and releases tension on the flexible members 240. The swaying motion modulation device 250 enables control over the amount and/or direction of swaying. Although the swaying motion modulation device 250 is shown in FIG. 2 as being coupled to a spring 240D, it is understood that an analogous swaying motion modulation device may be situated around the inner circumference of the outer hub 220 to compress and release tension on a flexible material embodiment of the flexible members 240 (e.g., the flexible material 240C).

In some embodiments, the swaying motion modulation device 250 may be controlled by the carrier assembly device controller 132. In some embodiments, a feedback loop is established between the physiological telemetry sensors 144 and the device controller 132 of FIG. 1B and the swaying motion modulation device 250 of FIG. 2. Such feedback loop may be tuned to provide a desired level of soothing, to minimize the amount of time until the infant falls asleep, etc. It is noted that the swaying apparatus 210 may be incorporated into structures of the infant soothing carrier assembly other than the wheel 200 for the purpose of imparting soothing acceleration components between the various structures of the carrier assemblies 10 and 100 of FIGS. 1A and 1B, respectively, and to an infant situated in the carrier 14.

Soothing motion-generating apparatus other than the swaying apparatus 210 may be included in the infant soothing carrier assembly 10. Such apparatus may include spring and/or gas cylinder suspensions, servo motors with offset cams to generate periodic swaying motion, solenoids to generate small acceleration components at particular locations, vibrating apparatus to generate soothing vibrations, etc.

Figure 3:
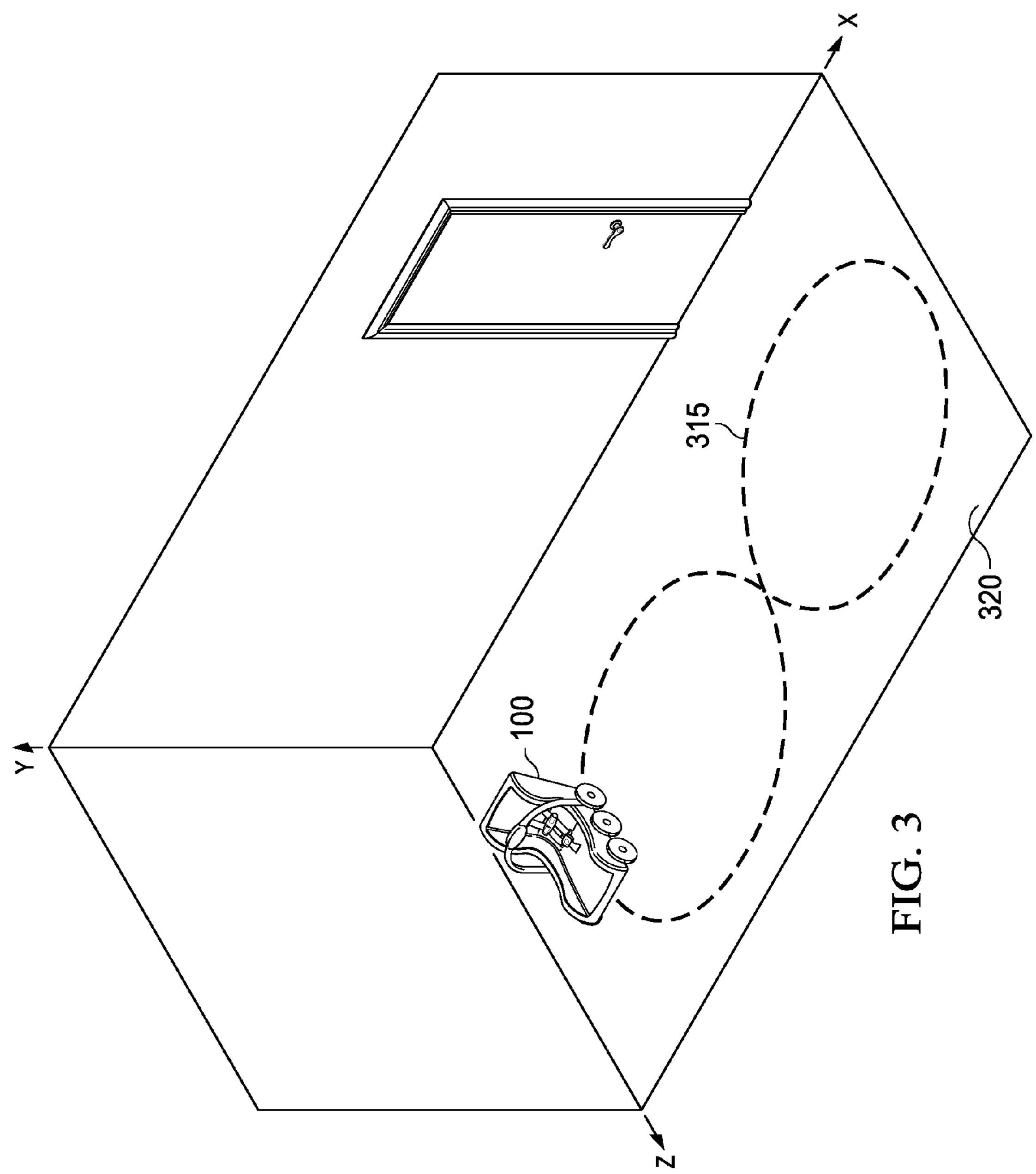
FIG. 3 is an illustration of an infant soothing carrier assembly according to various example embodiments.

FIG. 3 is an illustration of an infant soothing carrier assembly 100 according to various example embodiments. The infant soothing carrier assembly 100 includes a steering mechanism (e.g., the steering mechanism 128 as described with reference to FIG. 1B). The soothing carrier assembly 100 is programmed to proceed along a fixed path (e.g., the path 315) within a selected two-dimensional (2-D) space 320 (X,Z)

In some embodiments, the shape of the fixed path 315 may be determined by a device controller (e.g., the device controller 132 of FIG. 1B). The shape of the fixed path 315 may be user-selectable, as determined by the design of the controller 132. It is noted that, although the 2-D space 320 is shown in FIG. 3 as being located indoors, embodiments herein are not so limited.

Figure 4:
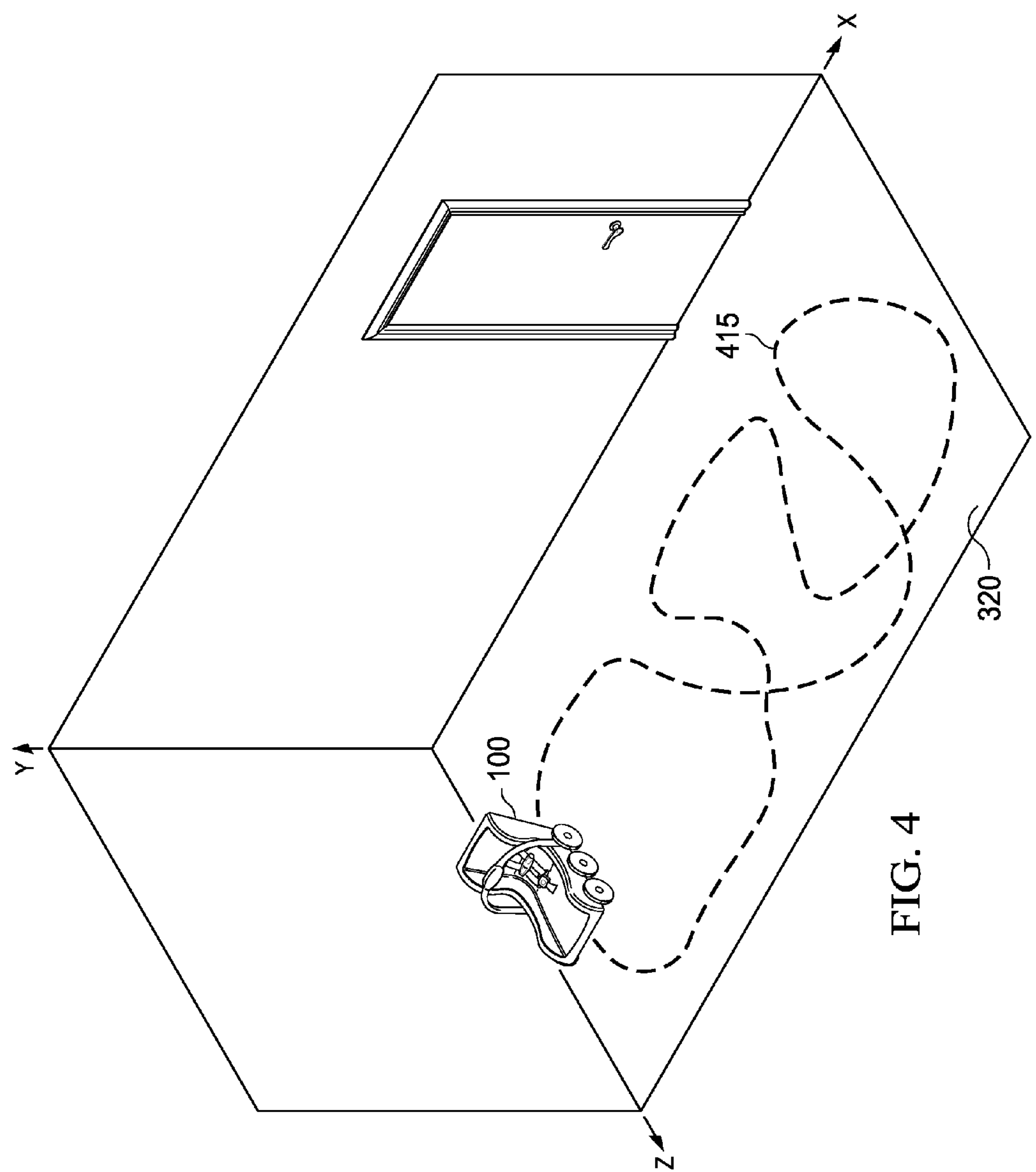
FIG. 4 is an illustration of an infant soothing carrier assembly according to various example embodiments.

FIG. 4 is an illustration of an infant soothing carrier assembly 100 according to various example embodiments. The infant soothing carrier assembly 100 includes a steering mechanism 128 (not shown) and sensors (e.g., the sensors 140 of FIG. 1B) and is capable of self-locomotion along a random path 415 within a selected 2-D space 320

An adaptive feedback loop may be established via the soothing device controller 132 of FIG. 1B. The sensors 140 detect the location and/or proximity of the soothing carrier assembly 100 relative to walls or other obstacles and provide that data as inputs to the device controller 132. The device controller 132 uses the position data to control the steering mechanism 128 such as to avoid detected obstacles by redirecting the soothing carrier assembly 100 along a different path.

Figure 5:
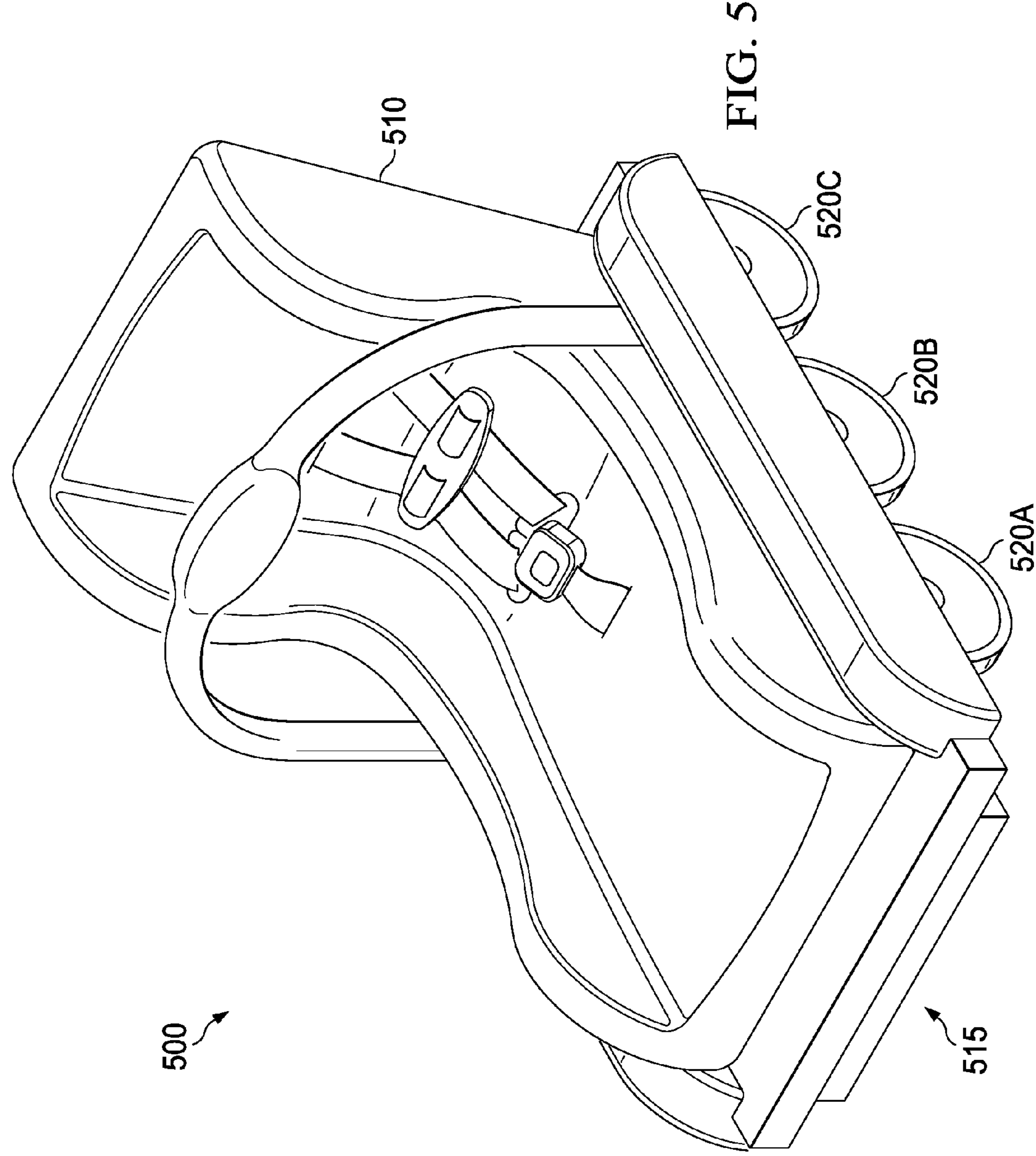
FIG. 5 is an illustration of an infant soothing carrier assembly according to various example embodiments.

FIG. 5 is an illustration of an infant soothing carrier assembly 500 according to various example embodiments. The soothing carrier assembly 500 includes a platform assembly 515 with wheels (e.g., the wheels 520A, 520B, and 520C, which may include the swaying mechanism 210 of FIG. 2 or similar). In some embodiments, the soothing carrier assembly 500 may include an infant carrier 510 mounted on the platform assembly 515. In some embodiments, the platform assembly 515 may be adapted to accept a snap-in infant carrier 510, including perhaps a consumer's choice of infant carriers. The infant soothing carrier assembly 500 is capable of self-locomotion along a path between points within a selected space In some embodiments, various components shown in FIG. 1B and previously described as being located within or upon the soothing carrier assembly 100 may instead be located within or upon the platform assembly 515. Such components may include the battery 114, the electric motor 118, the drivetrain 122, the steering mechanism 128, the soothing device controller 132, the mechanical linkage 136, the sensors 140, the speakers 142, the telemetry sensors 144, and/or the roll bars 154. In some embodiments, the speakers 142 and/or the telemetry sensors 144 may be located in or upon the infant carrier 510. The platform assembly 515 may be configured with a lock-in mechanism to accept a consumer's choice of infant carriers.

Figure 6:
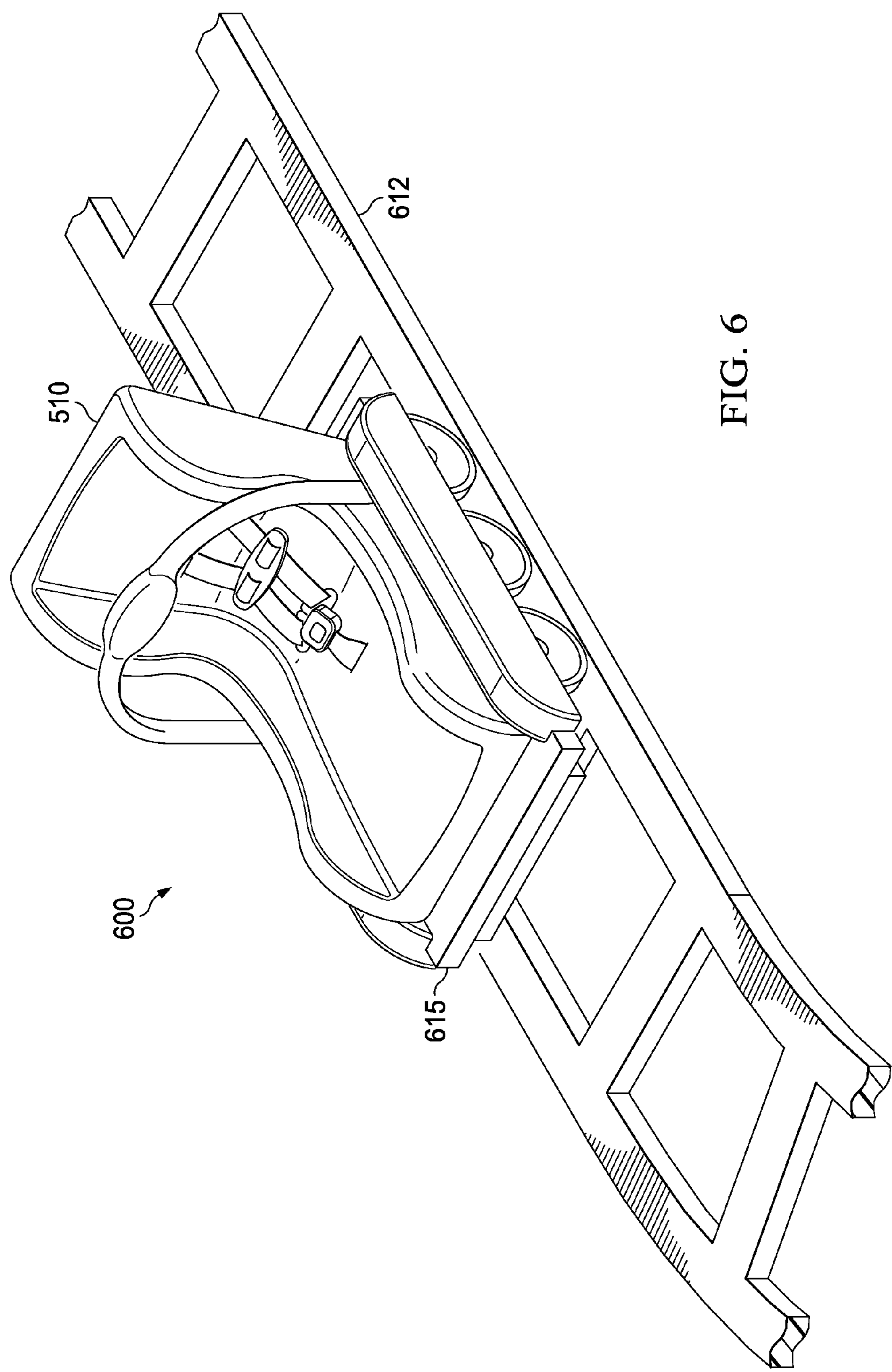
FIG. 6 is an illustration of an infant soothing carrier assembly according to various example embodiments.

FIG. 6 is an illustration of an infant soothing carrier assembly 600 capable of traveling along a track 612 according to various example embodiments. The infant soothing carrier assembly 600 includes a platform assembly 615 with wheels (e.g., the wheels 520A, 520B, and 520C of FIG. 5). In some embodiments, the carrier assembly 600 may include an infant carrier 510 mounted on the platform assembly 615. In some embodiments, the platform assembly 615 may be adapted to accept a snap-in infant carrier 510, including perhaps a consumer's choice of infant carriers.

The platform assembly 615 may (but need not) include the battery 114, the electric motor 118, the drivetrain 122, the soothing device controller 132, the speakers 142, the telemetry sensors 144, and/or the roll bars 154 as previously described with reference to the infant soothing carrier assembly 100 of FIG. 1B. In some embodiments, the speakers 142 and/or the telemetry sensors 144 may be located in or upon the infant carrier 510. Steering components may be omitted from the infant carrier soothing assembly 600, given that the assembly 600 is configured to travel along the track 612.

Figure 7:
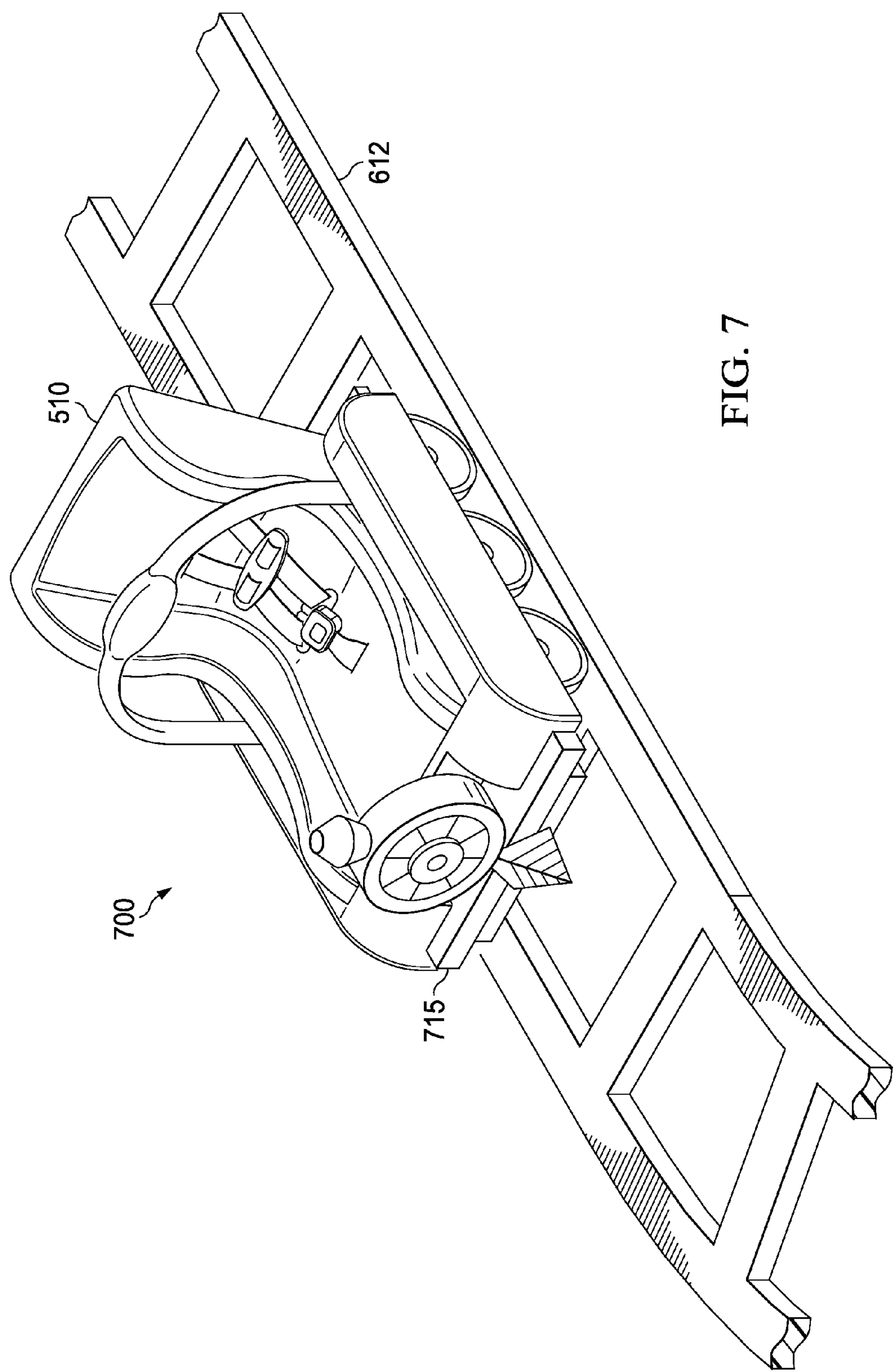
FIG. 7 is an illustration of an infant soothing carrier assembly according to various example embodiments.

FIG. 7 is an illustration of an infant soothing carrier assembly 700 according to various example embodiments. The infant soothing carrier assembly 700 is capable of traveling along a track 612 according to various example embodiments. The infant soothing carrier assembly 700 includes a toy motif platform assembly 715 with wheels (e.g., the wheels 520A, 520B and 520C of FIG. 5). In some embodiments, the carrier assembly 700 may include an infant carrier 510 mounted on the toy motif platform assembly 715. In some embodiments, the platform assembly 715 may be adapted to accept a snap-in infant carrier 510, including perhaps a consumer's choice of infant carriers.

The toy motif platform assembly 715 may include the battery 114, the electric motor 118, the drivetrain 122, the soothing device controller 132, the speakers 142, the telemetry sensors 144, and/or the roll bars 154 as previously described with reference to the infant soothing carrier assembly 100 of FIG. 1B. In some embodiments, the speakers 142 and/or the telemetry sensors 144 may be located in or upon the infant carrier 510. Steering components may be omitted from the infant soothing carrier assembly 700, given that the carrier assembly 700 is configured to travel along the track 612.

Figure 8:
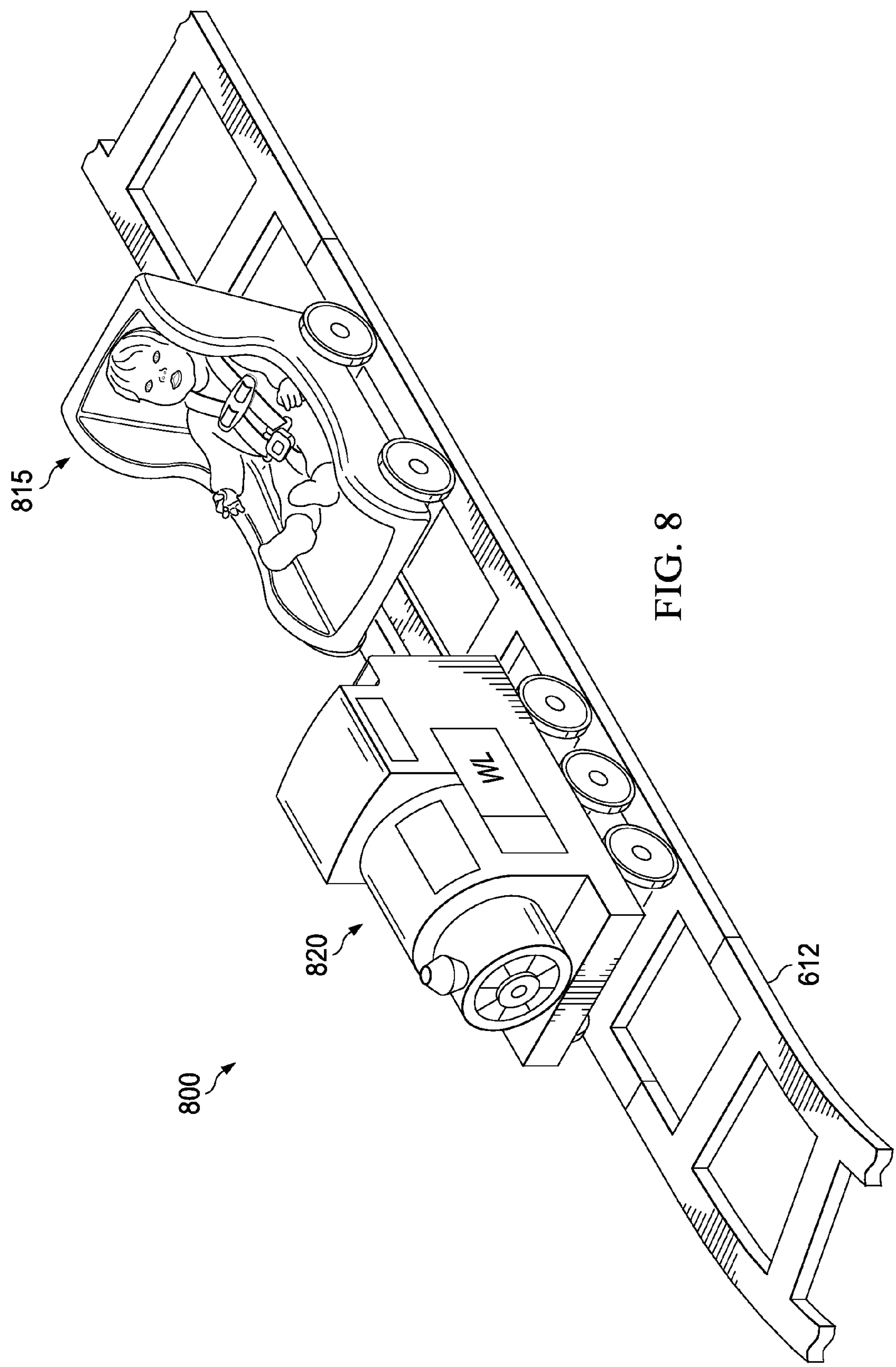
FIG. 8 is an illustration of an infant soothing toy assembly according to various example embodiments.

FIG. 8 is an illustration of an infant soothing toy assembly 800 according to various example embodiments. The soothing toy assembly 800 includes an infant soothing carrier 815 with wheels (e.g. the wheels 110A, 110B, and 110C of FIG. 1B). Some embodiments may alternatively include the rolling platform of FIG. 6 with a snap-in infant carrier as the infant soothing carrier 815. A snap-in seat may be substituted for the carrier when the infant outgrows the carrier. The soothing toy assembly 800 is configured to travel along a small-scale train track 612. The infant soothing carrier 815 is capable of being pulled or pushed by a train car 820 along the track 612. In a simple embodiment, an infant may be soothed by the clickety-clack sound and vibrations of the wheels as they pass over track segment junctions, coupled with a repetitive field of view of relatively long periodicity.

In a more complex embodiment, the infant soothing carrier 815 may include the soothing device controller 132, speakers 142, telemetry sensors 144, and/or roll bars 154 as previously described with reference to the infant soothing carrier assembly 100 of FIG. 1B. Steering components may be omitted from the infant soothing toy assembly 800, given that the toy assembly 800 is configured to travel along the track 612.

Figure 9:
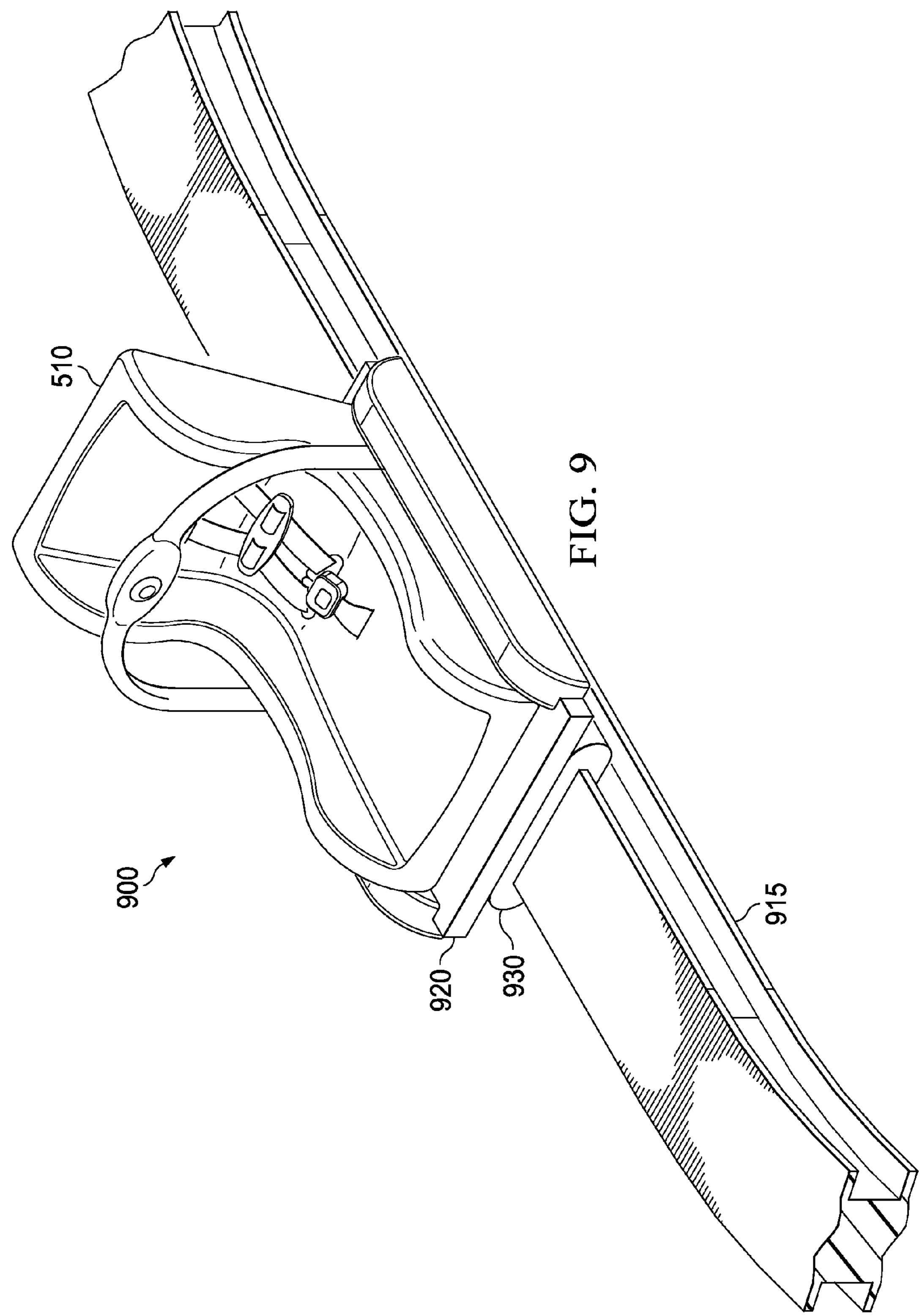
FIG. 9 is an illustration of an infant soothing carrier assembly according to various example embodiments.

FIG. 9 is an illustration of an infant soothing carrier assembly 900 according to various example embodiments. The carrier assembly 900 is configured to travel along a monorail 915. The carrier assembly 900 includes a monorail platform 920. In some embodiments, the carrier assembly 900 may include an infant carrier 510 mounted on the monorail platform assembly 920. In some embodiments, the monorail platform assembly 920 may be adapted to accept a snap-in infant carrier 510, including perhaps a consumer's choice of infant carriers.

The monorail platform 920 may include the battery 114, the electric motor 118, a monorail drivetrain, the soothing device controller 132, the speakers 142, the telemetry sensors 144, and/or the roll bars 154 as previously described with reference to the infant soothing carrier assembly 100 of FIG. 1B. In some embodiments, the speakers 142 and/or the telemetry sensors 144 may be located in or upon the infant carrier 510. Steering components may be omitted from the monorail platform 920, given that the infant soothing monorail assembly 900 is configured to travel along the monorail 915.

A monorail slide mechanism 930 couples the monorail platform 920 to the monorail 915. In some embodiments, a swaying suspension apparatus (not shown in FIG. 9) may be coupled between the monorail platform 920 and the monorail slide mechanism 930. The swaying suspension apparatus may include springs, flexible connecting materials such as rubber, etc. In some embodiments, the swaying suspension apparatus may be coupled to the device controller 132 via one or more servos, solenoids, etc. The latter configuration permits tuning of the swaying motion component of the soothing stimulus, and may operate in a closed loop with the telemetry sensors 144 as previously described with reference to the infant soothing carrier assembly 100 of FIG. 1B.

Figure 10:
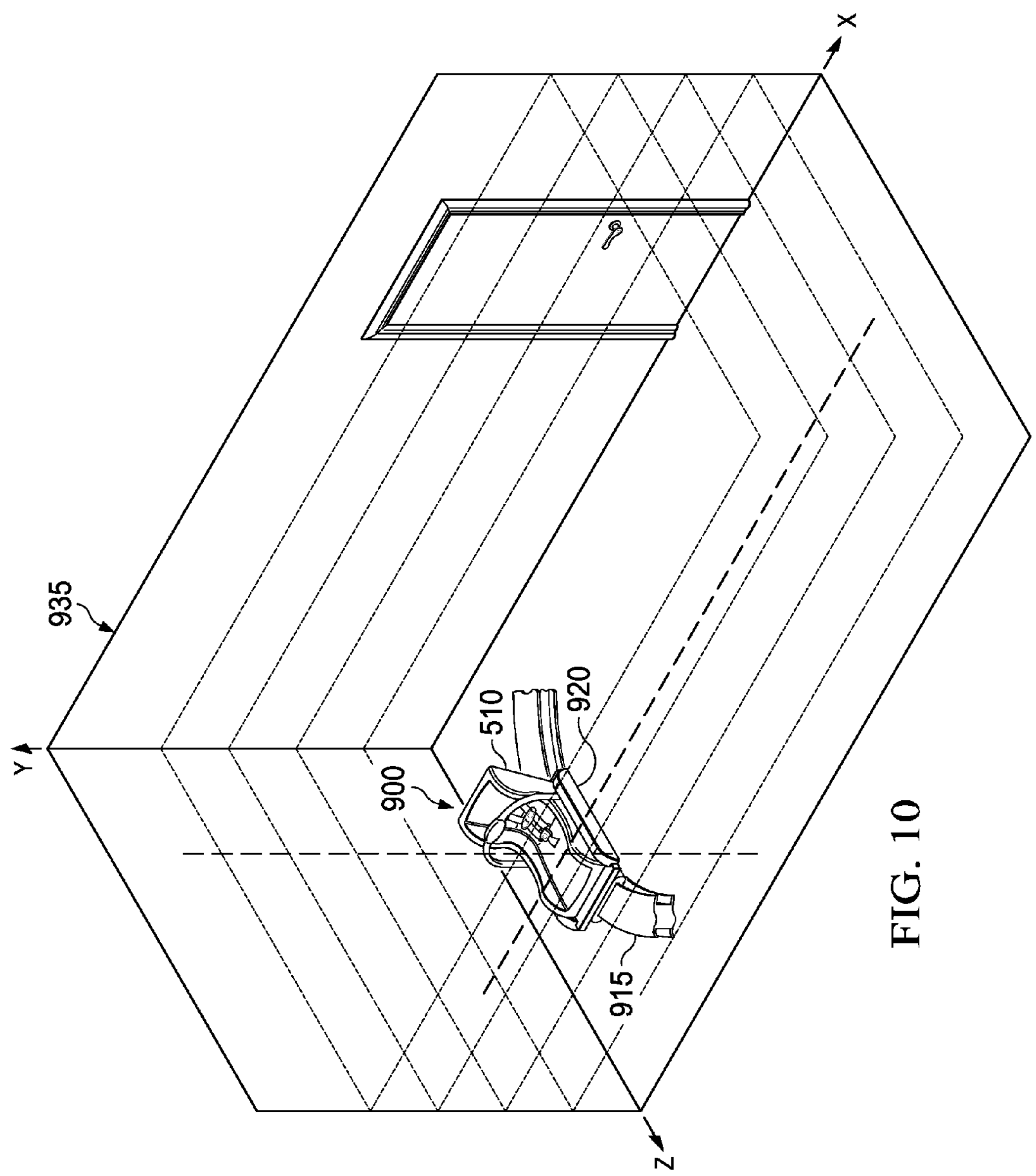
FIG. 10 is an illustration of an infant soothing carrier assembly according to various example embodiments.

FIG. 10 is an illustration of an infant soothing carrier assembly 900 according to various example embodiments. The carrier assembly 900 is capable of self-locomotion along a monorail 915 within a selected three dimensional (3-D) space 935 (X,Y,Z). In some embodiments, the monorail assembly 900 may include a crash cage (not shown in FIG. 10) coupled to the monorail platform 920. Some embodiments of the monorail assembly 900 may include a tether (not shown in FIG. 10) capable of being loosely coupled between one or more components of the monorail assembly 900 and an overhead support member such as a ceiling joist. Such tether may also be coupled to a harness capable of supporting an infant in case of failure of the infant soothing monorail assembly 900 and/or the monorail 915.

Figure 11:
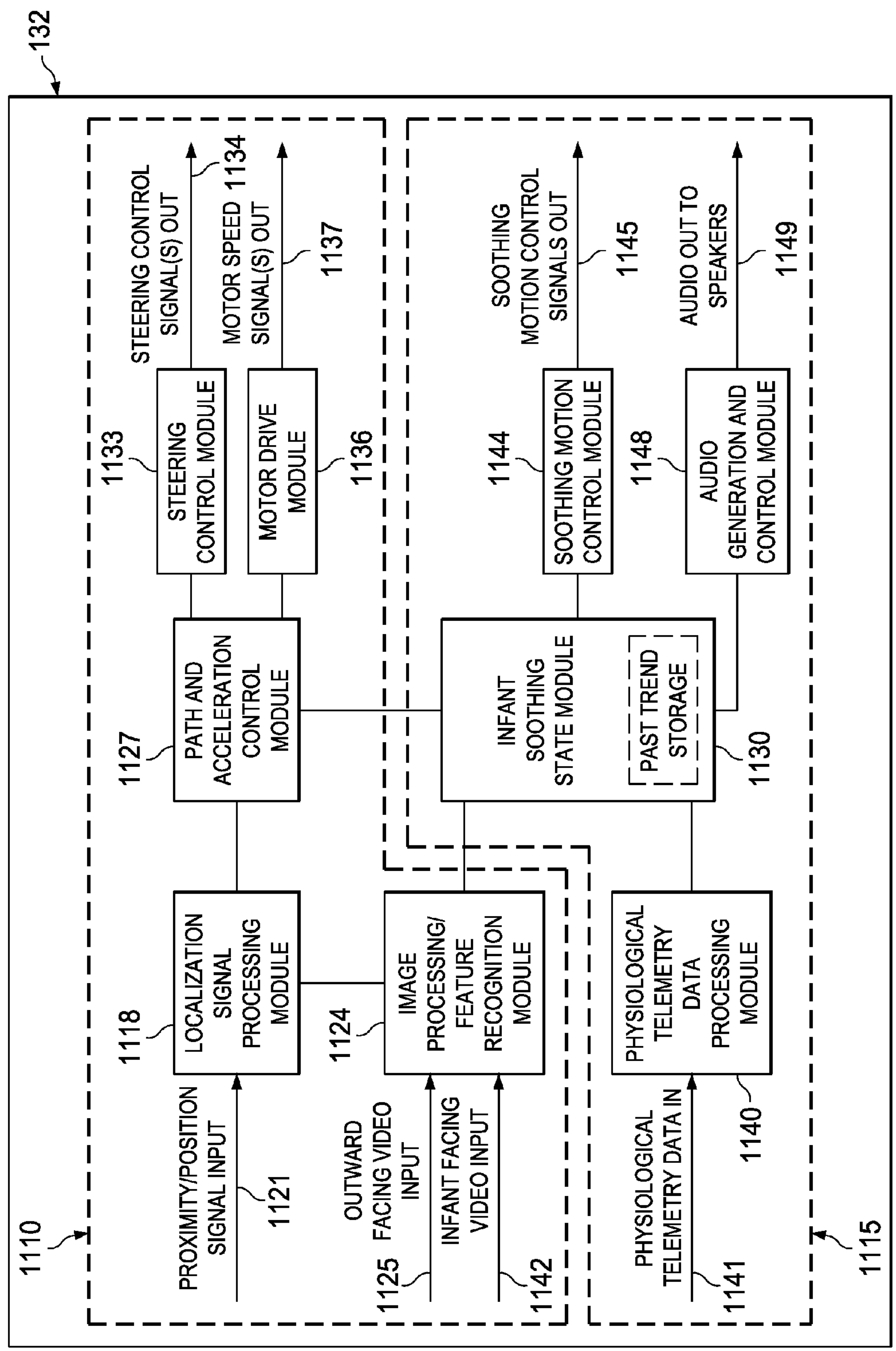
FIG. 11 is a block diagram of an infant soothing carrier assembly device controller according to various example embodiments.

FIG. 11 is a block diagram of an infant soothing carrier assembly device controller 132 according to various example embodiments. The controller 132 includes a path control section 1110. The path control section 1110 steers trackless embodiments of the infant soothing carrier assembly 10 of FIG. 1A and/or the infant soothing carrier assembly 100 of FIG. 1B along a proximate path. The path control section 1110 also controls acceleration of the various embodiments of the infant soothing carrier assemblies 10 and/or 100. In some embodiments, the controller 132 may also include an infant soothing control section 1115. The soothing control section 1115 outputs signals to soothing motion control apparatus (e.g., the swaying apparatus 210 of FIG. 2) and outputs soothing audio signals to speakers located at the infant soothing carrier assemblies 10 and/or 100.

The path control section 1110 includes a localization signal processing module 1118. The localization signal processing module 1118 analyzes sensor input data to determine the current position of the infant soothing carrier assemblies 10 and/or 100 with respect to the surroundings.

The localization signal processing module 1118 receives proximity and/or positioning input signals 1121 from sensors (e.g. the sensors 140 of FIG. 1B) at the infant soothing carrier assemblies 10 and/or 100. The input signals 1121 may carry echolocation data indicating the position of the infant soothing carrier assemblies 10 and/or 100 relative to surrounding objects. In some embodiments, the input signals 1121 may carry Doppler shift data to indicate the relative speed between the infant soothing carrier assemblies 10 and/or 100 and surrounding objects. The localization signal processing module 1118 may also receive GPS coordinate data and/or data associated with short range triangulation based upon wireless signals such as Wi-Fi, Bluetooth, personal area network (PAN), etc. signals.

An image processing and feature recognition module 1124 may be coupled to the localization signal processing module 1118. The image processing and feature recognition module 1124 receives an image signal 1125 from an outward-facing camera affixed to or integrated into some embodiments of the infant soothing carrier assemblies 10 and/or 100 (e.g., the camera 141A of FIG. 1B). The image signal 1125 may carry one or more single frame images or a video image sequence. The module 1124 may also receive image information 1142 from an infant-facing camera affixed to or mounted on the infant soothing carrier assemblies 10 and/or 100.

The module 1124 analyzes the received image information for features (e.g., shapes, colors, brightness, contrast, etc.) that can be used to identify surrounding objects such as walls, furniture, toys, persons, pets, etc. The image processing and feature recognition module 1124 sends object identification information to the localization signal processing module 1118 to aid in the localization of the infant soothing carrier assemblies 10 and/or 100 with respect to the surroundings.

The soothing device controller 132 also includes a path and acceleration control module 1127 coupled to the localization signal processing module 1118. The path and acceleration control module 1127 receives information associated with the position of the infant soothing carrier assemblies 10 and/or 100 relative to surrounding objects from the localization signal processing module 1118. The path control and acceleration module 1127 also receives information related to the emotional state of the infant from an infant soothing state module 1130, as further described below. The path and acceleration control module 1127 uses one or more of such inputs to determine the proximate path and acceleration of trackless embodiments of the infant soothing carrier assemblies 10 and/or 100. The path and acceleration control logic module 1127 uses one or more of the aforesaid inputs to determine rates of acceleration and deceleration in the case of tracked embodiments of the infant soothing carrier assemblies 10 and/or 100.

The soothing device controller 132 further includes a steering control module 1133 coupled to the path and acceleration control module 1127. The steering control module receives proximate path information from the path and acceleration control module 1127 and generates steering control output signals 1134. The steering control output signals 1134 operate on one or more of the steering mechanisms previously described with reference to FIG. 1B (e.g., the steering mechanism 128, pivoting versions of the wheels 110, etc.) to implement the desired proximate path.

A motor drive module 1136 is also coupled to the path and acceleration control module 1127. The motor drive module sends motor speed control signals 1137 to the motor(s) driving the wheels of the infant soothing carrier assemblies 10 and/or 100.

The controller 132 may also include an infant soothing control section 1115 to generate soothing motion control signals and soothing audio signals, as previously mentioned. The infant soothing control section 1115 may include a physiological telemetry data processing module 1140. The processing module 1140 receives physiological telemetry data 1141 from a set of physiological sensors (e.g., the sensors 144 of FIG. 1B) and/or sensor data acquisition devices located at the infant soothing carrier assemblies 10 and/or 100. Such telemetry may include body temperature, pulse rate, respiratory data, electrocardiographic data, electroencephalographic data, etc. The physiological telemetry data processing module 1140 analyzes the telemetry to estimate the current emotional state of the infant and passes such information to the infant soothing state module 1130.

The infant soothing state module 1130 is also coupled to the image processing feature recognition module 1124. The image processing feature recognition module 1124 receives image data 1142 from an infant-facing camera affixed to or integrated into the infant soothing carrier assemblies 10 and/or 100 (e.g., the camera 141B of FIG. 1B). The infant soothing state module 1130 may use feature data associated with the infant as well as feature data associated with the outward-facing video stream 1125, showing features within the infant's field of view, to further assess and predict the emotional state of the infant.

Using its estimate of the current emotional state of the infant together with stored past trend data, the infant soothing state module 1130 makes decisions about how to tune soothing motion, the proximate path of the infant soothing carrier assemblies 10 and/or 100, the acceleration/deceleration of the infant soothing carrier assemblies 10 and/or 100, and/or the magnitude and character of soothing audio out.

A soothing motion control module 1144 is coupled to the infant soothing state module 1130. Under control of the infant soothing state module 1130, the soothing motion control module 1144 outputs signals 1145 to soothing motion control apparatus (e.g., the swaying apparatus 210 of FIG. 2).

An audio generation control module 1148 is also coupled to the infant soothing state module 1130. Under control of the infant soothing state module 1130, the audio generation and control module 1148 outputs soothing audio signals 1149 to speakers located at the infant soothing carrier assemblies 10 and/or 100.

The infant soothing control section 1115 thus operates to establish a physiological feedback path. The soothing control section 1115 adjusts path control and acceleration, soothing motion control, and/or audio outputs based upon the current physiological state of an infant riding in the soothing apparatus. Such adjustments may then modify the emotional state of the infant. The infant soothing state module 1130 may be programmed to be adaptive and to make continuous adjustments as necessary in order to calm the infant or to put him or her to sleep. For example, as physiological telemetry from the infant indicates that the infant is falling into deeper sleep, some embodiments may respond by decreasing the magnitude and/or change other characteristics of soothing motions such as swaying, decrease the volume and/or change the sounds of soothing audio, etc. Likewise, if the physiological telemetry indicates that the infant is distressed, the magnitudes of soothing outputs may be increased and other characteristics tuned.

It is noted that the example embodiment of the infant soothing controller 132 as described above may be modified with additional or fewer sensory input modules and additional or fewer soothing stimulus output modules as may be deemed appropriate for various embodiments of infant soothing carrier assemblies 10, 100, 500, 600, 700, 800, and 900. Example embodiments of the soothing controller 132 are meant to convey the general idea of implementing a soothing motion oriented biofeedback system in order to sooth an infant and/or assist him or her in falling asleep.

Modules and components described herein may include hardware circuitry, optical components, single or multiprocessor circuits, and/or memory circuits. In some embodiments, such modules and components may also include computer-readable media with computer instructions encoded therein/thereon capable of being executed by a processor. Such computer-readable media may include nonvolatile memory with firmware stored therein, excluding non-functional descriptive matter. Components described herein may be combined, as desired by the architects of the infant soothing carrier assemblies 10, 100, 500, 600, 700, 800, and 900; the swaying wheel 200 and apparatus 210; and the device controller 132 and as appropriate for particular implementations of various embodiments.

Apparatus described herein may be useful in applications other than infant soothing. Examples of the infant soothing carrier assemblies 10, 100, 500, 600, 700, 800, and 900; the swaying wheel 200 and apparatus 210; and the device controller 132 are intended to provide a general understanding of the structures of various embodiments. They are not intended to serve as complete descriptions of all elements and features of apparatus and systems that might make use of these structures.

Apparatus described herein drive an infant carrier through space while providing soothing acceleration and/or sonic components. Some embodiments may incorporate biofeedback mechanisms to adaptively pinpoint characteristics of soothing motions and sounds appropriate to a selected soothing task for a particular infant in a particular emotional state. Infant caretakers may be relieved of time and energy consuming low-level soothing tasks as a result.

By way of illustration and not of limitation, the accompanying figures show specific embodiments in which the subject matter may be practiced. It is noted that arrows at one or both ends of connecting lines are intended to show the general direction of electrical current flow, data flow, logic flow, etc. Connector line arrows are not intended to limit such flows to a particular direction such as to preclude any flow in an opposite direction. The embodiments illustrated are described in sufficient detail to enable those skilled in the art to practice the teachings disclosed herein. Other embodiments may be used and derived therefrom, such that structural and logical substitutions and changes may be made without departing from the scope of this disclosure. This Detailed Description, therefore, is not to be taken in a limiting sense. The breadth of various embodiments is defined by the appended claims and the full range of equivalents to which such claims are entitled.

Such embodiments of the inventive subject matter may be referred to herein individually or collectively by the term "invention" merely for convenience and without intending to voluntarily limit this application to any single invention or inventive concept, if more than one is in fact disclosed. Thus, although specific embodiments have been illustrated and described herein, any arrangement calculated to achieve the same purpose may be substituted for the specific embodiments shown. This disclosure is intended to cover any and all adaptations or variations of various embodiments.

What is claimed is:

1. An infant soothing carrier assembly, comprising:

an infant carrier capable of self-locomotion;

a set of wheels rotatively coupled to the infant carrier to provide support for rolling motion along a path between points within a selected space and to transfer soothing vibrations and swaying motions to the infant carrier as the infant carrier moves along the path;

a device controller communicatively coupled to the set of wheels to perform at least one of determining the path, controlling navigation along the path, controlling magnitudes of the soothing vibrations and swaying motions, and monitoring an infant in the infant carrier;

a steering mechanism coupled to the set of wheels to control a direction of travel by setting an angle between at least one wheel position and a current direction of travel; and an electromechanical device coupled to the steering mechanism to impart motion to the steering mechanism responsive to signals from the device controller.

2. The infant soothing carrier assembly of claim 1, further comprising:

a drivetrain mechanically coupled to at least one wheel of the set of wheels;

an electric motor coupled to the drivetrain to provide mechanical power to the drivetrain; and a battery coupled to the electric motor to provide electrical power to the electric motor.

3. The infant soothing carrier assembly of claim 1, further comprising:

an electric motor mechanically coupled to at least one wheel to provide direct drive to the wheel; and a battery coupled to the electric motor to provide electrical power to the electric motor.

4. The infant soothing carrier assembly of claim 1, the electromechanical device being at least one of a servo motor or a solenoid.

5. The infant soothing carrier assembly of claim 1, further comprising:

an electric motor mechanically coupled to at least two wheels to provide direct drive to the wheels and to effect steering of the infant soothing carrier assembly by rotating the wheels at a differential rate; and a battery coupled to the electric motors to provide electrical power to the electric motors.

6. The infant soothing carrier assembly of claim 1, further comprising:

at least one position sensor coupled to the device controller to sense a distance between the infant soothing carrier assembly and a surrounding object.

7. The infant soothing carrier assembly of claim 1, further comprising:

at least one outward-facing camera mounted on or in the infant soothing carrier assembly and coupled to the device controller to provide video or frame-on-demand scene information to object feature recognition logic within the device controller.

8. The infant soothing carrier assembly of claim 1, further comprising:

at least one infant-facing camera mounted on or in the infant soothing carrier assembly and coupled to the device controller to provide video or frame-on-demand images of an infant situated in the infant carrier to facial feature recognition logic within the device controller and/or to an infant caretaker via a wireless link.

9. The infant soothing carrier assembly of claim 1, further comprising:

at least one loudspeaker or other sound-emitting transducer situated on or incorporated into the infant soothing carrier assembly and coupled to the device controller to emit soothing sounds.

10. The infant soothing carrier assembly of claim 1, further comprising:

at least one physiological telemetry sensor situated on or incorporated into the infant soothing carrier assembly and coupled to the device controller to monitor vital signs and provide input to determine at least one of an emotional state or a state of wakefulness of an infant in the carrier.

11. The infant soothing carrier assembly of claim 1, the device controller further comprising:

a path control section to generate steering and locomotion speed control information and to steer the infant soothing carrier assembly along a proximate path at a selected rate; and an infant soothing control section communicatively coupled to the path control section to generate soothing motion control signals and soothing audio signals, to send the soothing motion control signals to soothing motion generating apparatus, and to send the soothing audio signals to a sound transducer.

12. The infant soothing carrier assembly of claim 11, the path control section further comprising:

a localization signal processing module to receive at least one of distance information from a proximity sensor, position information from a position sensor, or environmental feature information derived from scenes captured by an outward facing camera;

a path and acceleration control module communicatively coupled to the localization signal processing module to perform obstacle avoidance operations and to generate path and speed information associated with at least one of a fixed path or a random path;

a steering control module communicatively coupled to the path and acceleration control module to generate steering control signals and to send the steering control signals to an electromechanical device capable of imparting motion to a steering mechanism; and a motor drive module to generate motor speed signals and to send the motor speed signals to at least one drive motor.

13. The infant soothing carrier assembly of claim 11, the path control section further comprising:

a path and acceleration control module to generate path and speed information associated with a selected path;

a steering control module communicatively coupled to the path and acceleration control module to generate steering control signals associated with the selected path and to send the steering control signals to an electromechanical device capable of imparting motion to a steering mechanism; and a motor drive module to generate motor speed signals and to send the motor speed signals to at least one drive motor.

14. The infant soothing carrier assembly of claim 11, the infant soothing control section further comprising:

an infant soothing state module to determine a current desired soothing motion control state and a current desired soothing audio state;

a soothing motion control module communicatively coupled to the infant soothing module to receive an input from the infant soothing state module indicating the desired soothing motion control state, to generate soothing motion control signals corresponding to the desired soothing motion control state, and to send the soothing motion control signals to soothing motion generating apparatus; and an audio generation and control module communicatively coupled to the infant soothing state module to receive an input from the infant soothing state module indicating the current desired soothing audio state, to generate soothing audio signals corresponding to the desired soothing audio state, and to send the soothing audio signals to at least one audio output transducer.

15. The infant soothing carrier assembly of claim 14, the infant soothing control section further comprising:

an image processing and feature recognition module communicatively coupled to the path and acceleration control section and to the infant soothing state module to accept image signals from at least one of an outward-facing camera or an infant-facing camera, to extract feature information from the image signals, and to send the feature information to at least one of the path control section or to an infant soothing state module associated with the infant soothing section; and a physiological telemetry data processing module communicatively coupled to the infant soothing state module to receive physiological telemetry data associated with an infant situated in the infant soothing carrier assembly from at least one physiological telemetry sensor, to determine an emotional state of the infant from the physiological telemetry data, and to send information associated with the infant emotional state to the infant soothing state module.

16. The infant soothing carrier assembly of claim 1, at least one wheel of the set of wheels further comprising:

a swaying apparatus wheel hub component to control a degree of rigidity of mechanical coupling between the wheel and a point of fixation of the wheel to the infant carrier and to impart soothing lateral acceleration components as the infant soothing carrier assembly moves along the path.

17. The infant soothing carrier assembly of claim 16, the swaying apparatus wheel hub further comprising:

an outer hub affixed to the wheel; and an inner hub flexibly coupled to the outer hub to allow relative movement between the inner hub and the wheel.

18. The infant soothing carrier assembly of claim 17, the swaying apparatus wheel hub further comprising:

at least one flexible member to flexibly couple the outer hub to the inner hub, the flexible member being at least one of a solid flexible material, a set of springs, or a set of springs embedded in the solid flexible material.

19. The infant soothing carrier assembly of claim 18, the swaying apparatus wheel hub further comprising:

a swaying motion modulation device coupled to the flexible member to compress and release tension on the flexible member to control an amount of swaying motion.

20. The infant soothing carrier assembly of claim 1, at least one wheel of the set of wheels further comprising:

an irregular segment around the outer circumference of the wheel to impart soothing vertical acceleration components as the wheel rotates.

* * * * *